US00PP07990P

United States Patent [19]

Richardson

[11] Patent Number: Plant 7,990

[45] Date of Patent: Sep. 29, 1992

[54] "AUTUMN ROSE" PEACH TREE

[76] Inventor: Roy D. Richardson, Rte. 2, Box 520, Bakersfield, Calif. 93307

[21] Appl. No.: 680,245

[22] Filed: Apr. 1, 1991

[51] Int. Cl.[5] ..... A01H 5/00

[52] U.S. Cl. ..... Plt./43.2

[58] Field of Search ..... Plt./43

[56] References Cited

U.S. PATENT DOCUMENTS

P.P. 3,582 8/1974 Merrill ..... Plt. 43

*Primary Examiner*—James R. Feyrer

*Attorney, Agent, or Firm*—Worrel & Worrel

[57] ABSTRACT

A new and distinct variety of peach tree which is closely similar to the "Autumn Gem" peach tree (U.S. Plant Pat. No. 3,582), of which it is a mutation, but from which it is distinguished by producing fruit which are mature for harvesting and shipment approximately four weeks later than the fruit of the "Autumn Gem" peach tree.

1 Drawing Sheet

BACKGROUND OF THE NEW VARIETY

The present invention relates to a new and distinct variety of peach tree which will hereinafter be denominated varietally as the "Autumn Rose" peach tree and, more particularly, to a peach tree which produces fruit which are mature for commercial harvesting and shipment approximately November 1st to November 20th near Arvin in the Southern San Joaquin Valley of California, and which further is distinguished by producing a large red fruit, the flesh of which is of a light amber-yellow coloration, is firm and crisp, and which is otherwise closely similar to the late peach tree "Autumn Gem" (U.S. Plant Pat. No. 3,582), of which the new variety is a mutation, with the exception that it ripens approximately four weeks later than the "Autumn Gem" peach tree.

The ripening date of the fruit of commercial varieties of peach trees is frequently the single most significant criterion in determining their success in the marketplace. With the multitude of varieties of peach trees, both patented and unpatented, early and late ripening varieties are frequently of particular value.

In some instances, varieties have been developed which are closely similar in all other characteristics to well accepted commercial varieties, but ripen significantly earlier or later than those varieties. The market acceptance of such new varieties may be substantially enhanced over other varieties ripening approximately during the same time period, but not possessing any such relationship. The new variety of the present invention bears such a strong resemblance to the "Autumn Gem" peach tree (U.S. Plant Pat. No. 3,582) and yet ripens approximately four weeks later than the fruit of the "Autumn Gem" peach tree.

ORIGIN AND ASEXUAL REPRODUCTION OF THE NEW VARIETY

The present variety of peach tree was discovered in 1986 by the applicant in his orchard which is located near Arvin in Kern County in the Southern San Joaquin Valley of California. The applicant discovered the newly found seedling as a mutation of the "Autumn Gem" peach tree (U.S. Plant Pat. No. 3,582). In 1988, the new variety was asexually reproduced at the applicant's direction and the resulting trees of the new variety were planted in 1989 in another of the applicant's orchards approximately one-half mile from the location of the parent tree near Arvin in Kern County. The asexually reproduced trees were observed by the applicant and first bore fruit in 1990. The applicant has closely examined the asexually reproduced trees of the new variety and confirmed that they are identical to the parent tree.

SUMMARY OF THE NEW VARIETY

The "Autumn Rose" peach tree is characterized as to novelty by producing a large red fruit which has good flavor and firmness, ripening for commercial harvesting and shipment approximately November 1st to November 20th in the Southern San Joaquin Valley of California. The new and novel variety is very closely similar to the "Autumn Gem" peach tree (U.S. Plant Pat. No. 3,582), of which "Autumn Rose" peach tree is a mutation, but from which it is distinguished and characterized principally as to novelty by producing fruit which are ripe for harvesting and shipment approximately four weeks later than the fruit of the "Autumn Gem" peach tree.

BRIEF DESCRIPTION OF THE DRAWING

The drawing is a color photograph showing fruit of the new variety of the present invention including a first sectioned to show the pit in position in the pit well; a second sectioned and with the pit removed to expose the pit well; a third shown in side elevation to reveal the suture; a fourth shown in bottom plan view to reveal the apex; and a fifth shown in top plan view to expose the stem cavity; and foliage typical of the new variety.

DETAILED DESCRIPTION

Referring more specifically to the pomological details of this new and distinct variety of peach tree, the following has been observed under the ecological conditions prevailing at the orchard of origin which is located near Arvin, Calif. of Kern County. All major color code designations are by reference to the Dictionary of Color, by Maerz and Paul, Second Edition, 1950. Common color names are also employed occasionally.

TREE

Generally:
- *Size.*—Normal for peach tree.
- *Vigor.*—Vigorous.
- *Figure.*—Upright to upright-spreading with general form and density.
- *Productivity.*—Productive.
- *Regularity of bearing.*—Regular.

Trunk:
- *Size.*—Average.
- *Surface texture.*—Quite rough with above average amounts of scarfskin present.
- *Color.*—Burnt Umber brown (15-A-12).
- *Lenticel.*—Openings — Moderately calloused. Light brown colored callous tissue present, Terrapin (14-B-10). Numbers — Medium amount. Size — Large. Form — Flat.

Branches:
- *Size.*—Normal.
- *Surface texture.*—Normal.
- *Color.*—One year or older wood — Medium Malay brown (15-C-11). A substantial amount of russet and checking is present on the more mature wood. Current season's shoots — Light grey-green (Piguant green 20-K-6). When exposed to direct sunlight, shoots are tinged with red (Saraband red 6-K-8).
- *Surface texture—current season's shoots.*—Relatively smooth and glabrous.

LEAVES

Size:
- *Generally.*—Very large.
- *Average length.*—22.6 cm (8.889 inches).
- *Average width*—4.0 cm (1.574 inches).

Form: Linear lanceolate. Quite narrow in relation to their length.

Color:
- *Upwardly disposed surface.*—Dark green (23-L-5).
- *Downwardly disposed surface.*—Lighter green (22-K-7).
- *Leaf midvein.*—The under side is a light yellow-green (19-K-4).

Marginal form:
- *Generally.*—Crenate in form with large, broad and moderately deep crenations. Most crenations are tipped with a brown trichome. Crenations at mid-margin are often double in form.

Leaf:
- *Margin.*—Moderately undulate.
- *Apex.*—Acuminate in form, with the tip most often twisted sideways.

Petiole:
- *Size.*—Moderately long.
- *Length.*—11 mm (0.433 inches) to 16 mm (0.629 inches).
- *Thickness.*—2.0 mm (0.078 inches).
- *Color.*—Light green (piguant green 20-K-6).

Stem glands:
- *Form.*—Large.
- *Number.*—Variable, from 3 to 7.
- *Position.*—Alternate.
- *Pattern.*—Most frequently two or three large glands are present on the base of the leaf margin in alternate position and two more additional glands are present further up on the leaf margin. Occasionally a gland is present on the leaf petiole itself, but most are borne on the basal portion of the leaf blade.
- *Type.*—Variable. Most glands are of the reniform type, but an occasional globose gland is not uncommon.

Basal gland:
- *Color.*—Light yellow-green (18-L-5) when young. There is darkening and deterioration with age.

Stipules: No stipules present at the time of description.

FLOWERS

Flower Buds:
- *Width.*—6.35 mm (4/16 inches).
- *Length.*—7.93 mm (5/16 inches).
- *Surface texture.*—Normal for peach tree.

Flowers — generally: Typical for peach tree.
- *Date of bloom.*—February 26 through March 5.
- *Width.*—14.27 mm (9/16 inches).
- *Length.*—15.87 mm (10/16 inches).

Petals:
- *Color.*—Red.

FRUIT

Maturity when described: Ripe for commercial harvesting and shipment approximately November 1st to November 20th near Arvin in Kern County in the Southern San Joaquin Valley of California.

Size:
- *Generally.*—Uniform and large.
- *Average diameter in cheek.*—79 mm (3.110 inches).
- *Average diameter in the axial plane.*—75 mm (2.952 inches).
- *Average diameter transverse in the suture plane.*—76 mm (2.992 inches).
- *Average diameter transverse and at right angles to the suture plane.*—About 76 mm (2.992 inches).
- *Form.*—Uniformity — Broadly ovate to nearly globose in lateral aspect. Nearly globose in axial aspect. Symmetry — Symmetrical.
- *Suture.*—Generally — A distinct raised line from apex to base. The suture is substantially calloused and rough. Most often the suture is red in color and very distinct, although occasionally the coloration can be somewhat less pronounced.
- *Ventral surface.*—Generally — Rounded, except for the raised suture. One side is often slightly lipped.
- *Stem cavity.*—Generally — Oval and moderately deep. Cavity shoulders often show the indentation of the branch on which the fruit was borne. The ventral suture is slightly folded within the cavity basin. Width — 30 mm (1.181 inches). Depth — 13 mm (0.511 inches) to 16 mm (0.629 inches). Length — 36 mm (1.417 inches). Shape — Normal.
- *Stem.*—Generally — Medium. Length — 9 mm (0.354 inches) to 12 mm (0.472 inches). Thickness — 3.5 mm (0.137 inches). Color — Greenish-brown (14-L-4).
- *Base.*—Slightly truncate. Base angle usually very oblique to fruit axis, shorter on the ventral suture side.
- *Apex.*—Shape — Generally — Rounded with a very low tip.
- *Pistil point.*—Variable, from perfectly apical to very oblique. A depression is usually present on both the ventral and dorsal side of the apex.

Skin:

*Thickness.*—Medium and relatively tenacious to the flesh at commercial maturity.

*Flavor.*—Mild in flavor without much acidity.

*Pubescence.*—Pubescent with a short and fine pubescence.

*Texture.*—Normal.

*Tendency to crack.*—None.

*Blush color.*—Can cover from 15 to 60 percent of fruit surface, with fruit exposed to direct sunlight in the highest range. Blush pattern is variable, but most often is in a streaked and mottled pattern. The darkest areas of blush are an Egyptian red (6-L-11) and are usually part of the mottled pattern. Red blush color lightens to an Ember red (5-K-10).

*Ground color.*—Amber yellow (10-J-3). A red ventral suture line is usually present (Withered Rose 5-J-10).

Flesh:

*Flesh color.*—Light amber-yellow from the skin inward (10-K-3).

*Surface of pit cavity.*—Normal.

*Color of pit well.*—Medium Korea red (5-J-11). A substantial amount of red coloration radiates outwards from the pit cavity some 15 mm (0.590 inches) to 20 mm (0.787 inches) into the flesh.

*Juice production.*—Juicy.

*Flavor.*—Very good flavor. Well balanced and pleasant.

*Aroma.*—Moderate in amount and pleasant.

*Texture.*—Firm and crisp at commercial maturity.

*Fibers.*—Numbers — Moderate number. Size — Moderately long. Texture — Tender. Color — Light colored.

*Ripening.*—Even.

*Eating quality.*—Very good.

Stone:

*Attachment.*—A full freestone. The stone fills the stone cavity very well. Almost no air space is present in the cavity.

*Fibers.*—Numbers — Few. The fibers are usually most evident basally. Length — Short.

*Size.*—Generally — Medium. Length — Average 37 mm (1.456 inches). Width — 25 mm (0.984 inches). Thickness — 19 mm (0.748 inches).

*Form.*—Generally — Most frequently oval.

*Apex.*—Shape — Generally — Rounded with an acute, dentate tip.

*Color.*—Dry — Variable, from a tan brown (12-G-7) darkening to a medium brown (14-G-11).

*Base.*—Shape — Variable. Usually rounded to slightly truncate. Angle — Very oblique to the stone axis.

*Apex.*—Generally rounded in form with an acute, dentate tip.

*Sides.*—Generally — Most frequently slightly unequal.

*Hilum.*—Medium to slightly below average in size and oval in form. The hilum is well defined and enclosed by a smooth raised collar.

*Surface.*—Moderately rough with the deepest grooves present over the apical shoulders laterally. The entire stone surface is finely pebbled or covered with small pock marks, giving the surface a roughened appearance.

*Ventral edge.*—Moderately wide with two to four low wings coalesced basally and converging apically. The ventral edge is moderately pitted over the entire surface.

*Dorsal edge.*—Moderately narrow with a distinct but narrow groove from the base to about mid-stone. Above mid-stone to the apex, the groove is reduced to a narrow line. The apical shoulder of the dorsal suture is substantially eroded.

*Ridges.*—Along the dorsal edge are cut in several locations by cross grooves.

*Tendency to split.*—None.

Use: Fresh market use. It has potential for use in local markets and also for long distance shipping.

Keeping quality: Excellent.

Shipping and handling qualities: Excellent.

Although the new variety of peach tree possesses the described characteristics noted above as a result of the growing conditions prevailing near Arvin, Calif., Kern County, in the central part of the San Joaquin Valley of central California, it is to be understood that variations of the usual magnitude and characteristics incident to changes in growing conditions, irrigation, fertilization, pruning and pest control are to be expected.

Having thus described and illustrated my new variety of peach tree, what I claim as new and desire to be secured by Plant Letters Patent is:

1. A new and distinct variety of peach tree substantially as illustrated and described and which is closely similar to the "Autumn Gem" peach tree (U.S. Plant Pat. No. 3,582), producing large freestone fruit of a yellow ground color and a streaked and mottled red blush coloration, but from which it is distinguished and characterized principally as to novelty by producing such fruit which are mature for commercial harvesting and shipment approximately November 1st to November 20th in the Southern San Joaquin Valley of central California.

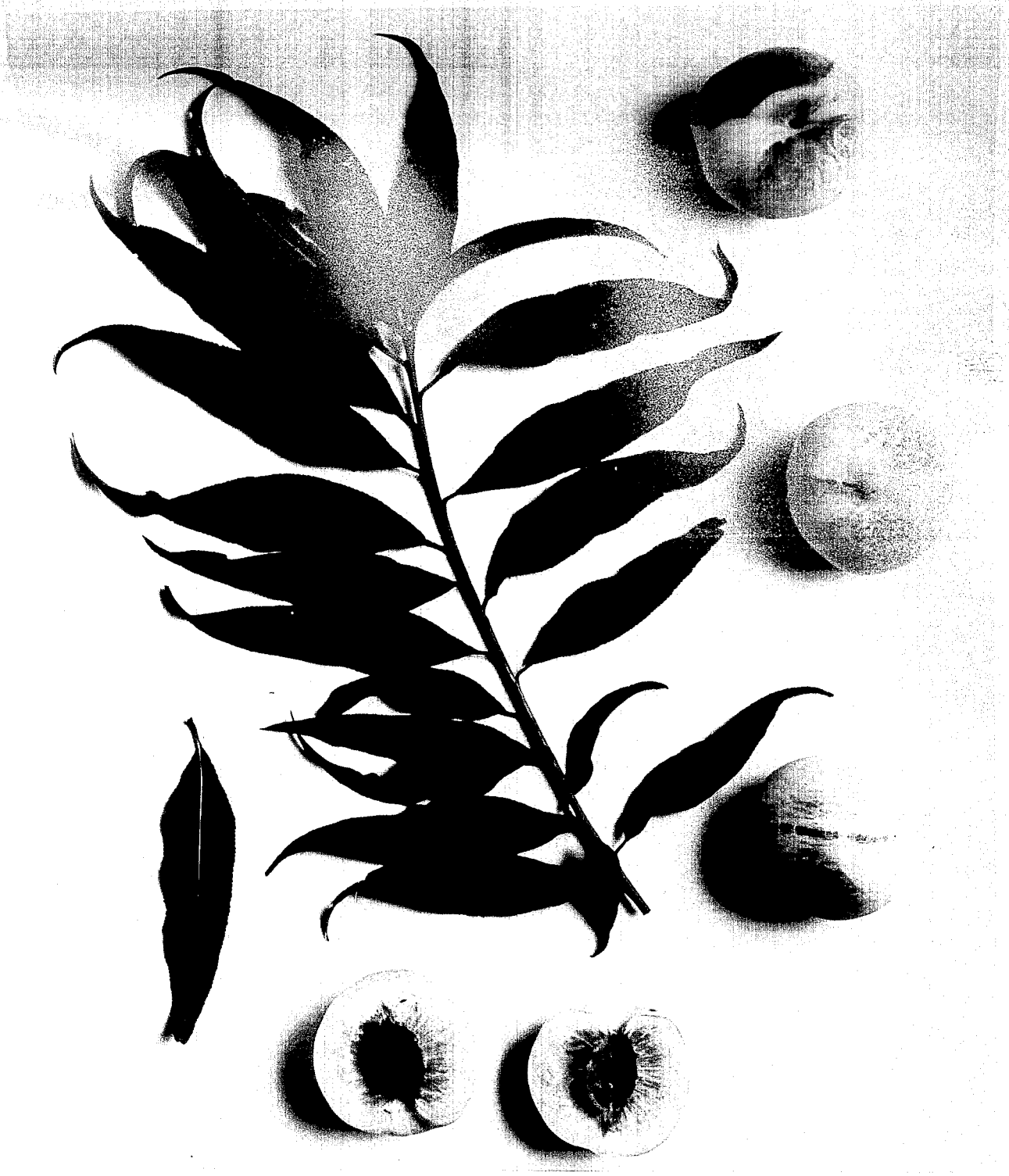

* * * * *